(12) United States Patent
Fernandez

(10) Patent No.: US 7,988,918 B2
(45) Date of Patent: Aug. 2, 2011

(54) STRUCTURES FOR ENHANCED DETECTION OF FLUORESCENCE

(75) Inventor: Andres Fernandez, San Francisco, CA (US)

(73) Assignee: Complete Genomics, Inc., Mountain View, CA (US)

( * ) Notice: Subject to any disclaimer, the term of this patent is extended or adjusted under 35 U.S.C. 154(b) by 225 days.

(21) Appl. No.: 12/261,447

(22) Filed: Oct. 30, 2008

(65) Prior Publication Data

US 2009/0117006 A1 May 7, 2009

Related U.S. Application Data

(60) Provisional application No. 60/984,652, filed on Nov. 1, 2007.

(51) Int. Cl.
*G01N 21/64* (2006.01)
(52) U.S. Cl. .................................. 422/82.08
(58) Field of Classification Search ............... 422/82.08
See application file for complete search history.

(56) References Cited

U.S. PATENT DOCUMENTS

| | | |
|---|---|---|
| 4,284,897 A | 8/1981 | Sawamura et al. |
| 5,091,652 A | 2/1992 | Mathies |
| 5,296,700 A | 3/1994 | Kumagai |
| 5,381,224 A | 1/1995 | Dixon et al. |
| 5,504,336 A | 4/1996 | Noguchi |
| 5,552,272 A | 9/1996 | Bogart |
| 5,646,411 A | 7/1997 | Kain et al. |
| 5,672,880 A | 9/1997 | Kain |
| 5,834,758 A | 11/1998 | Trulson et al. |
| 5,847,400 A | 12/1998 | Kain et al. |
| 6,008,892 A | 12/1999 | Kain et al. |
| 7,227,633 B2 | 6/2007 | Kraus et al. |
| 2007/0099208 A1 | 5/2007 | Drmanac et al. |
| 2007/0188746 A1 | 8/2007 | Kraus et al. |
| 2009/0130703 A1 * | 5/2009 | Wagner et al. ............ 435/29 |

FOREIGN PATENT DOCUMENTS

WO    WO 02/48691 A1    6/2002
WO    WO 2004106902 A1 * 12/2004

OTHER PUBLICATIONS

International Preliminary Report on Patentability and Written Opinion corresponding to the PCT application No. PCT/US2008/082084, date of mailing May 14, 2010, 6 pages total.
International Search Report PCT/US08/82084 dated Jan. 26, 2009.

* cited by examiner

*Primary Examiner* — Bobby Ramdhanie
(74) *Attorney, Agent, or Firm* — Kilpatrick Towsend & Stockton LLP; Kenneth R. Allen

(57) ABSTRACT

Substrates are provided for use in the detection, identification and analysis of biologic or chemical samples that are labeled with a fluorescent label, in which the plane of maximum fluorescence is displaced from a reflective substrate surface so that the intensity maximum of the standing wave interference pattern of incident and reflected probe radiation is enhanced. The format of the substrates includes substantially planar surfaces as well as substrates with introduced variations to the substrate surface, e.g., depressions, wells, pedestals and the like, disposed in arrays or other similar structures such that one or more fluorophore-comprising objects can be attached thereto.

17 Claims, 6 Drawing Sheets

STRUCTURES FOR ENHANCED DETECTION OF FLUORESCENCE

CROSS-REFERENCES TO RELATED APPLICATIONS

The present application claims benefit under 35 USC 119(e) of U.S. provisional Application No. 60/984,652, filed on Nov. 1, 2007, entitled "Structures For Enhanced Detection Of Fluorescence," the content of which is incorporated herein by reference in its entirety.

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK.

NOT APPLICABLE

BACKGROUND OF THE INVENTION

This invention relates to substrates for use in the fluorescent, phosphorescent or luminescent detection of biological or chemical samples. Fluorescence microscopy is often used in the fields of molecular biology, biochemistry and other life sciences for analyzing biological molecules, including nucleic acids (DNA, RNA) and proteins (enzymes, antigens, etc.) that have been tagged or labeled with fluorescent probes. One such use is DNA diagnostics, such as for gene detection, in which a DNA sample is deposited on and bound to a glass substrate. The bound DNA on the substrate can then be imaged by fluorescence. The fluorescence of a sample has in the past been manually assessed by visual inspection through a conventional microscope, but this manual method is time-consuming and costly. As an improvement, various automated fluorescence imaging systems are now available. However, the structures employed to provide an observation platform fail to take full advantage of the characteristics of the fluorescent probes.

An important aspect of fluorescence detection and measurement instruments is sensitivity, which is primarily determined by the signal-to-noise ratio (SNR) of the optical imaging system of the instrument. One obvious approach to increasing SNR, and thereby improving sensitivity, is to reduce background noise. Sources of background noise include specular or diffuse reflection of the fluorescence-stimulating laser light from the sample, autofluorescence of the substrate holding the sample, autofluorescence from the optics in the light path of the optical imaging system, stray light, and dark current of the detector. Both stray light and much of the reflected laser light can be rejected, while passing the fluorescent light, by using dichroic and other spectral filters and beam splitters in the system.

More recent approaches for enhancing detection involve the use of improved substrate surfaces. U.S. Pat. No. 6,008,892 to Kain et al. and WO 02/48691 to Chaton et al. disclose sample substrates which are reflective for specific excitation wavelengths. U.S. Pat. No. 7,227,633 to Kraus et al., further develops such technology by providing substrates with enhancement of the fluorescence signal for two or more different excitation wavelengths. However, each of these disclosures describes optimized substrates for the detection of samples that are at or substantially near the surface of the substrate. Detection using these substrates does not take into account the finite thickness of certain imaging samples, and thus are not optimized for samples in which the plane of maximum fluorescent signal differs from the surface.

It is helpful to understand certain terms of art. The terms used herein are intended to have the plain and ordinary meaning as understood by those of ordinary skill in the art. The following definitions are intended to aid in understanding the present invention but are not intended to vary or otherwise limit the meaning of such terms unless specifically indicated.

"Fluorophores" are any molecule comprising or consisting of a functional group that absorbs energy within a specific absorption spectrum and re-emits energy at a different (but equally specific) emission spectrum. Preferred fluorophores for use as markers in the present invention include, but are not limited to, fluorescein, cascade blue, hexachloro-fluorescein, tetrachloro-fluorescein, TAMRA, ROX, FAM, Cy3, Cy3.5, Cy5, Cy5.5, 4,4-difluoro-5,7-diphenyl-4-bora-3a,4a-diaza-s-indacene-3-propionic acid, 4,4-difluoro-5,p-methoxyphenyl-4-bora-3a,4a-diaza-s-indacene-3-propionic acid, 4,4-difluoro-5-styryl-4-bora-3a,4-adiaz-a-S-indacene-propionic acid, 6-carboxy-X-rhodamine, N,N,N',N'-tetramethyl-6-carboxyrhodamine, Texas Red, Eosin, 4,4-difluoro-5,7-diphenyl-4-bora-3a,4a-diaza-s-indacene-3-propionic acid, 4,4-difluoro-5,p-ethoxyphenyl-4-bora-3a,4a-diaza-s-indacene 3-propionic acid and 4,4-difluoro-5-styryl-4-bora-3a,4a-diaza-S-indacene-ptopionic acid, the DyLight Fluor family available from Thermo Fisher Scientific of Waltham, Mass. and the Alexa Fluor family from Molecular Probes of Eugene, Oreg.

The terms "intensity maximum" and "intensity minimum" refer to specific intensities of the radiation (or light) pattern produced by the interference of incident light provided by an outside source with the light reflected from a substrate surface. As used in the context of the present invention detection, "intensity maximum" means at or substantially near the peak of the intensity profile of the radiation (or light) pattern. The term "intensity minimum" used in the context of fluorophore detection means at or substantially near the trough of the intensity profile of the radiation (or light) pattern.

"Solid support" and "support" are used interchangeably and refer to a material or group of materials having a rigid or semi-rigid surface or surfaces. In many embodiments, at least one surface of the solid support will be substantially flat, although in some embodiments it may be desirable to physically separate regions on the support with, for example, wells, raised regions, pedestals, etched holes, or the like. Microarrays usually comprise at least one planar solid phase support, such as a glass microscope slide.

SUMMARY OF THE INVENTION

According to the invention, substrates are provided for use in the detection, identification and analysis of biologic or chemical samples of non-zero thickness and that are labeled with a fluorescent label, in which the plane of maximum fluorescence is displaced from a reflective substrate surface so that the observed fluorescence is enhanced by the intensity maximum of the standing wave interference pattern of incident and reflected excitation and emission radiation. The format of the substrates includes substantially planar surfaces as well as substrates with introduced variations to the substrate surface, e.g., depressions, wells, pedestals and the like, disposed in arrays or other similar structures such that one or more fluorophore-comprising objects can be attached thereto.

In a particular aspect of the invention, the invention provides enhanced substrates with optical characteristics adapted for enhancing fluorescence detection and imaging of fluorophore-comprising structures that have a non-zero thickness, namely, a center of mass and/or radius greater than approximately 10 nm when resting on the top surface of an enhancement layer, where the enhancement layer is typically on the order of 100 nm thick.

A structure for enhancing fluorescence detection comprises a reflective substrate and a fluorescence enhancement layer, where the thickness of the fluorescence enhancement layer is optimized for the detection of fluorophore-comprising objects of non-zero thickness so that when disposed on the fluorescence enhancement layer, there is a plane of maximum fluorescence that is displaced from the surface of the fluorescent enhancement layer. The plane of maximum fluorescence for detection of specific objects on the fluorescence enhancement layer can be calculated or empirically determined for detection of one or more fluorophores under defined conditions and thickness of the fluorescence enhancement layer.

In many aspects of the invention, the fluorophore-comprising object is associated with a chemical or biological element present in or on the fluorescent enhancement layer. An example is a strand of DNA conveniently arranged in a sphere of non-zero thickness.

In an aspect of the invention, enhancing fluorescent detection of fluorophore-comprising objects is effected by a reflective substrate and a fluorescence enhancement layer, where the thickness of the fluorescence enhancement layer is optimized for the detection of fluorophore-comprising objects that, when disposed on the fluorescence enhancement layer, have a plane of maximum fluorescence that is measurably displaced from the surface of the fluorescent enhancement layer. The thickness of the fluorescent enhancement layer can be defined by determination of the plane of maximum fluorescence for the objects to be detected.

The plane of maximum fluorescence for detection of specific objects on the fluorescence enhancement layer can be defined (e.g., calculated or empirically determined) for a particular detection environment and fluorophore by determining the actual or estimated center of mass ($\delta$) and/or radius of the fluorophore comprising object, the specific conditions for detection (e.g., aqueous conditions, detection in air, etc.) and the reflective nature of the components of the device (e.g., the nature of the reflective substrate, a specific dielectric used in the fluorescent enhancement layer, and the like), the center of the absorption spectrum of the fluorophore of interest, and the center of the emission spectrum of the fluorophore.

In various aspects of the invention the fluorescence enhancement layer may be uniformly thick or have plurality of depression regions or have a plurality of raised regions, where the objects to be detected are disposed within the designated regions, such that the placement of the objects upon the fluorescence enhancement layer is optimized so that, the plane of maximum fluorescence of the objects is at an intensity maximum for detection.

An aspect of the invention is a device for enhancing fluorescent detection of fluorophore-comprising objects comprising a solid support and a fluorescence enhancement layer having a plurality of raised areas, where the objects to be detected are disposed on the raised areas, and where the placement of the objects on the fluorescence enhancement layer is optimized so that, when the objects are disposed on the raised areas of the fluorescence enhancement layer, the plane of maximum fluorescence of the objects is at an intensity maximum for detection of a fluorophore. Preferably in this aspect, the surface of the fluorescence enhancement layer below the raised areas is at an intensity minimum for detection of the fluorophore. Both the plane of maximum fluorescence for detection of the objects and the intensity minimum for the fluorescent substrate surface above the depressions can be calculated or empirically determined for optimal detection under particular conditions and the thickness of the structures of the fluorescence enhancement layer provided to maximize the detection of the fluorophore(s) while minimizing any background.

In certain preferred aspect of the various embodiments, the fluorescent enhancement layer of the substrate is made up of a thin, transparent, dielectric layer or a stack of thin, transparent, dielectric layers ensuring optimal transmission of the fluorescence signal. Such dielectric materials include, but are not limited to, the following materials: $SiO_2$, $TiO_2$, $Ta_2O_5$, $HfO_2$, $ZrO_2$, $MgO$, $Si_3N_4$, $MgF_2$ and $YF_3$.

In a specific aspects of the various embodiments of the invention where it is desirable to use multiple fluorophores (e.g., both Cy3 and Cy5), the enhancement layer thickness that will provide the most advantageous detection of the multiple fluorophores can be determined and used to determine the structure of the device. The thickness is optimized to produce the best overall detection of the fluorophores for a given excitation wavelength. The fluorescence intensity may be an average of the maximum intensity of the excitation/absorption wavelengths and the emission wavelengths of the fluorophores.

In a specific aspect, the invention preferably is a substrate comprising a flat reflecting surface over which a thin, dielectric layer of thickness (a) is provided, and on which the objects to be detected are disposed. The thickness (a) is carefully tuned so that the combined thickness of the object and the fluorescent enhancement layer provide a plane of maximum fluorescence at the peak of the intensity profile for a given fluorescence signal emitted by a fluorophore.

In specific embodiments, in which the fluorophores are distributed throughout the object, and assuming a uniform distribution of fluorophores, the plane of maximum fluorescence can be determined using the center of mass ($\delta$) of the object. In other embodiments, where the location of maximum fluorophore density on an object is known, the plane of maximum fluorescence can be directly calculated based on the positioning of the fluorophores.

In one aspect of the invention, a sample substrate of the invention is adapted for use with a single fluorescence excitation light, and the objects to be detected may each comprise a plurality of one fluorophore. The thicknesses of the layers is optimized for the detection of the objects to ensure that the plane of maximum fluorescence for detection of the fluorophore on said substrate is located near an antinode of a standing wave formed by the excitation light with the first wavelength incident on said substrate.

It is another important aspect of the present invention to provide a substrate having maximum enhancement of the fluorescence signal for two or more different excitation wavelengths. Thus, in a specific aspect of various embodiments, the present invention provides a sample substrate comprising application adjusted enhancement factors for two or more excitation wavelengths.

In a preferred embodiment, the thickness (a) of the fluorescence enhancement layer is carefully tuned to provide the optimum detection of two or more fluorophores by utilizing a thickness (a) that is selected for enhancement of an average intensity profile of two or more fluorophores.

It is an advantage of the invention that the fluorescent enhancement layer can be constructed to have wells or raised areas in/on which the objects are positioned. This provides placement of the object to provide an intensity maximum for detection of the objects, while the surfaces between the objects are positioned at an intensity minimum.

It is another advantage of the invention that the fluorescent enhancement layer can be provided as a series of pedestals on the reflective substrate, upon which the object is positioned. This also provides placement of the objects to provide an intensity maximum for detection of the objects, while the surfaces between the objects are positioned at an intensity minimum.

In specific aspects of varying embodiments, the different introduced surface structures (e.g., depressions, raised areas, pedestals, etc.) are substantially the same to accommodate objects of the same or similar size and/or mass.

In other specific aspects, the depressions or the raised areas of the fluorescence enhancement layer on a single device may vary, e.g., structures in a single device may have a varying thickness. Such depressions or raised areas may be designed to accommodate objects of different sizes on a single device or to account for differences in the plane of maximum fluorescence when two or more fluorophores are being used. This allows for maximum detection of objects of varying size or multiple fluorophores using single excitation parameters.

It is a feature of the invention that it provides optimized detection of objects for which the plane of maximum fluorescence differs from the substrate surface.

It is a further feature of the invention that the substrate surface can be positioned at an intensity minimum, this decreasing background signal.

These and other objects, advantages, and features of the invention will be apparent to those persons skilled in the art upon reading the details of the methods as more fully described below.

DETAILED DESCRIPTION OF THE INVENTION

Figure 1:
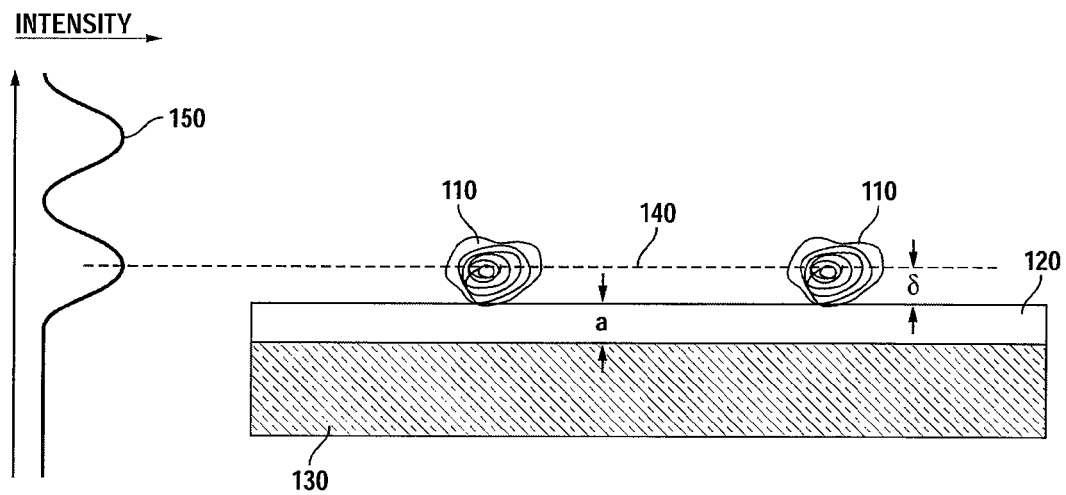
FIG. 1 is a schematic drawing illustrating the detection of an object comprising multiple fluorophores on an optimized substrate of the device of the invention.

The fluorescence efficiency for structures located at or near a reflective substrate can be strongly modified by the interference resulting from the interaction of light with the substrate. Fluorescent intensity can be directly related to specific phenomena related to their physical relationship with such a substrate. First, for any incident excitation power density, local intensity can be determined by the interference construction. This intensity can be enhanced by constructive interference or attenuated by destructive interference, so that the optimal average excitation rate of a biologic or chemical sample comprising multiple fluorescent molecules will depend in large part on the localization of the largest number such molecules in the interference field. Second, the emission rate of a fluorophore is also modified due to the interaction or "coupling" of the emitting fluorescent dipole with the non-infinite environment. Due to interference, the emission rate of each fluorophore can either be enhanced or attenuated.

The present invention takes advantage of such physical phenomena by utilizing a calculated constructive interference to determine the most advantageous substrate structure of a device for fluorescent detection. Specifically, the present invention provides a substrate surface constructed to account for the following physical phenomena: 1) the average distance of the greatest fluorescent emission of a fluorophore-comprising object, such as a bead or a DNA concatamer; 2) the thickness (a) of a fluorescence enhancing layer, such as a dielectric layer; 3) the average excitation wavelength of the fluorophore(s) to be used in detection of the object under particular conditions; and 4) the average emission wavelength of the fluorophore(s) to be used in detection of the object under particular conditions.

The improved substrate provides increased sample excitation and fluorescence emission by detection of the plane of maximum fluorescent of an object to be detected by providing a fluorescent enhancement layer (e.g., a dielectric layer) on a reflective surface (e.g., a metal surface) and optimization of a fluorescence enhancement layer (e.g., a transparent dielectric layer) to account for the finite size of the object. The thickness of the fluorescence enhancement layer can be calculated directly or empirically determined to be of a thickness to provide an intensity maximum of the interference pattern to increase the resulting fluorescent signal. The resulting electromagnetic field distribution connected to the excitation wavelength outside the sample substrate is optimally a standing wave or close to a standing wave with planes of nodes and planes of antinodes.

In the present invention, the fluorescent enhancement layer has a thickness selected so that the area of greatest fluorescence of a three-dimensional object (i.e., its plane of maximum fluorescence) is at a maximum of both the excitation and emission of the fluorophore.

In specific aspects of the various embodiments, the reflective substrate can be obtained using a metal surface (Kain et al., 1999) or using an all dielectric Bragg reflector comprising a stack of quarter wave pairs of dielectrics (e.g., $SiO_2$ and $Si_3N_4$), with the dielectric material having the lower optical refractive index also serving as the substrate of the fluorescence enhancement layer. As compared with a metallic mirror, the Bragg reflector has no optical losses and a great enhancement of the fluorescence can be achieved with a stack of alternate pairs of dielectrics.

In the present invention, the radius and/or center of mass ($\delta$) of the object containing the multiple fluorophore molecules is a critical aspect of determining the structure of the substrate, as spacing needs to be optimized for greatest intensity of fluorescence. When the fluorophores are present at or very near the reflective substrate surface, as with conventional oligonucleotide arrays, the plane of maximum fluorescence is substantially the surface itself, and the most appropriate thickness (a) of the fluorescence enhancement layer can be determined substantially by the equation:

$$a = \frac{1}{4}(\lambda/n)$$

where n is the index of refraction of the enhancement layer and $\lambda$ is the wavelength of light in a vacuum. The wavelength $\lambda$ selected is typically a weighted average of the peaks of the absorption spectrum and the emission spectrum, where the weighting is determined by the relative strength of absorption with respect to the emission amplitude.

As the fluorophores are preferably provided in objects with a center of mass measurably displaced from the substrate surface, the plane of maximum fluorescence will reflect the distribution of the fluorophores in or on the object in relation to the fluorescence enhancement layer surface. Thus, the plane of maximum fluorescence must be adjusted to account for the center of mass ($\delta$) of the fluorophore-comprising object:

$$a + \delta = \frac{1}{4}(\lambda/n)$$

where (a) is the thickness of the fluorescent enhancement layer, ($\delta$) is the center of mass of the object relative to the substrate surface, n is the index of refraction in the enhancement layer and $\lambda$ is the wavelength of light in a vacuum. It should be noted that this equation needs to be modified if the index of refraction above the enhancement layer is significantly different than the enhancement layer.

Where the object is substantially spherical, and the fluorophores are relatively evenly disposed on or through the object, the radius (r) can be used to calculate the plane of maximum fluorescence for the object. Thus, when optimizing the plane of maximum fluorescence for a spherical object on a surface, the following equation can be used:

$$a + r = \frac{1}{4}(\lambda/n)$$

where (a) is the thickness of the fluorescent enhancement layer, (r) is the non-zero radius of the object relative to the substrate surface, n is the index of refraction in the enhancement layer and $\lambda$ is the wavelength of light in a vacuum.

Device Construction

The devices of the present invention are composed of multiple layers, including at least the following: a reflective substrate and a fluorescence enhancement layer. The base may itself be composed of a reflective substrate, such as a metal or a Bragg reflector, or the base may provide a solid support on which the reflective substrate can be provided. Thus, devices of the invention optionally comprise a substrate base for the deposition of the reflective substrate, which can be made of substantially any material that can be coated. For example, the base material can be a transparent material such glass or plastic. In preferred aspects of the invention, the base is a material such as a silicon, aluminum, or titanium substrate, or such a coating upon a suitable substrate.

The fluorescent enhancement layer of the substrate may be made up of a thin, transparent, dielectric layer or a stack of thin, transparent, dielectric layers. Such dielectric materials include, but are not limited to, $SiO_2$, $TiO_2$, $Ta_2O_5$, $HfO_2$, $ZrO_2$, $MgO$, $Si_3N_4$, $MgF_2$ and $YF_3$.

In specific embodiments, the devices of the invention are constructed using multi-layer coating technologies. The optimization of the multilayer coating design can be done by applying one of the well known techniques in the art. The reflective substrate base may be coated, for example, by one of the following methods: thermal and/or electron beam vapor deposition, replication, transfer, film deposition, by processes of the CVD type (LPCVD, PECVD etc.) or of the PVD type such as sputtering, i.e., DC magnetron sputtering. Ion assisted deposition processes can be used as well as the sol-gel process. Layers of substrate are optionally transferred onto the base by bonding or molecular adhesion.

Etching can be provided by multiple available techniques, such as the damascene technique, whereby openings are selectively etched into a dielectric layer. Generally, a photoresist material is layered onto the dielectric layer and a pattern of openings outlined in the photoresist layer using lithographic techniques. An anisotropic etch is then used to form the openings in the dielectric layer. The photoresist material is then removed. Where multiple layers and depths are desired, such a process requires the use of more than one mask layer with varying resistances to the anisotropic etch processes.

In embodiments where depressions or raised areas in the fluorescence enhancement layer are desirable, multi-layer deposition on the reflective base may be used to produce structures in the fluorescent enhancement layer. For example, a multilayer dielectric fluorescence enhancement layer can be designed using a layer of a material with a higher refractive index e.g., $Si_3N_4$ (having a refractive index of n=2.0), disposed on a dielectric material with a lower optical refractive index such as $SiO_2$ (n=1.48). Other coating materials, including multilayer coatings comprising more than two materials, can be used as well.

FIG. 1 illustrates a first aspect of the present invention for the detection of an object comprising multiple fluorophores on an optimized substrate. In this aspect, objects to be detected 110 having a center of mass ($\delta$) are placed on the fluorescent enhancement layer 120 having a thickness (a). The fluorescent enhancement layer 120 is disposed on a reflective substrate 130. The thickness (a) of the fluorescent enhancement layer is designed so that when the objects 110 are placed on the substrate, the plane of maximum fluorescence 140 for a radiation (or light) pattern 150 is at the maximum intensity when using a selected incident light from an outside source.

Figure 2:
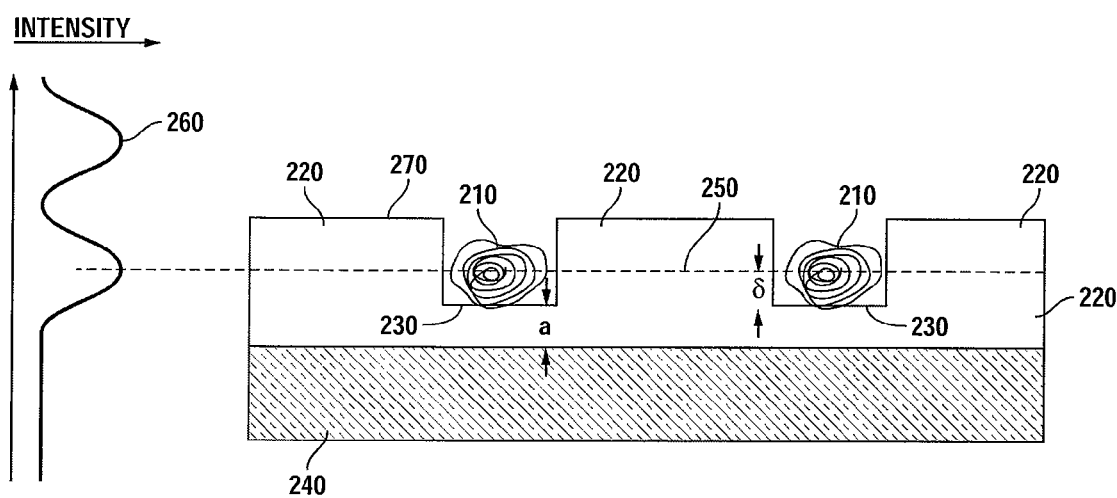
FIG. 2 is a schematic drawing illustrating the detection of an object comprising multiple fluorophores in on an optimized substrate comprising multiple depressions.

FIG. 2 illustrates a second aspect of the invention, in which objects are disposed on an optimized substrate comprising multiple depressions. In this aspect, objects to be detected 210 having a center of mass ($\delta$) are placed on the fluorescent enhancement layer 220 is composed of a single material (e.g., a dielectric) disposed on a reflective substrate 240, having a thickness (a) from the surface of the depressions 230 to the reflective substrate 240. The thickness (a) of the depressions of the fluorescent enhancement layer is designed so that when the objects 210 are placed on the substrate in the depressions, the plane of maximum fluorescence 250 for a radiation (or light) pattern 260 is at the maximum intensity when using a selected incident light from an outside source. The top surface of the fluorescence enhancement layer 270 is preferably at the minimum intensity for the incident light.

Figure 3:
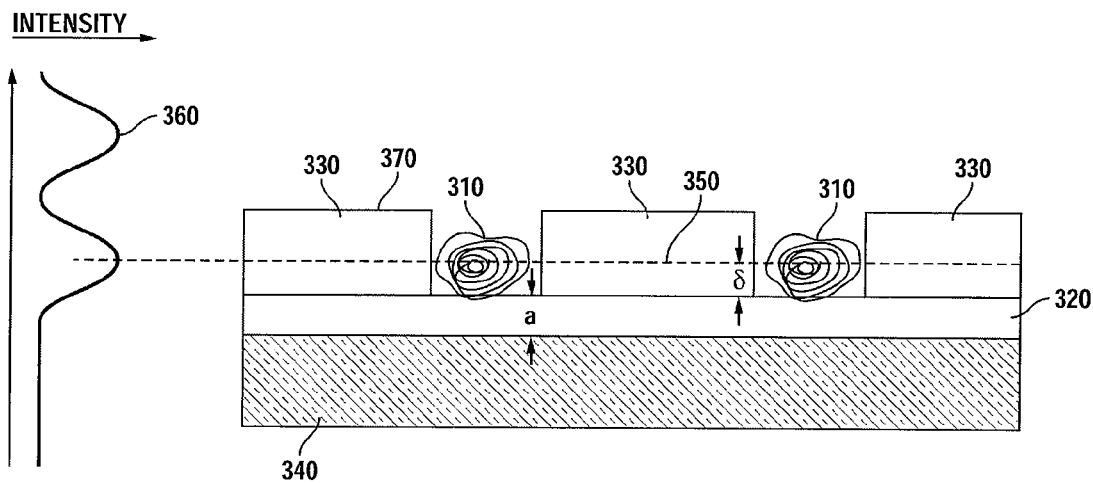
FIG. 3 is a schematic drawing illustrating the detection of an object comprising multiple fluorophores on an optimized substrate comprising a fluorescence enhancement layer and multiple depressions including a second material in the regions surrounding the depressions.

FIG. 3. illustrates a third aspect of the invention, in which objects are disposed on an optimized substrate comprising multiple depressions created using deposition of a second material over the dielectric material in the fluorescence enhancement layer. In this aspect, objects to be detected 310 having a center of mass ($\delta$) are placed on a fluorescent enhancement layer 320 is composed of a single material (e.g., a dielectric) disposed on a reflective substrate 340 having a thickness (a) from the surface of the depressions to the reflective substrate 340. The depressions are created through the deposition of a second material 330 using standard patterning techniques. The thickness (a) of the depressions of the fluorescent enhancement layer is designed so that when the objects 310 are placed on the substrate in the depressions, the plane of maximum fluorescence 350 for a radiation (or light) pattern 360 is at the maximum intensity when using a selected incident light from an outside source. The top surface of the fluorescence enhancement layer 370 is preferably at the minimum intensity for the incident light.

Figure 4:
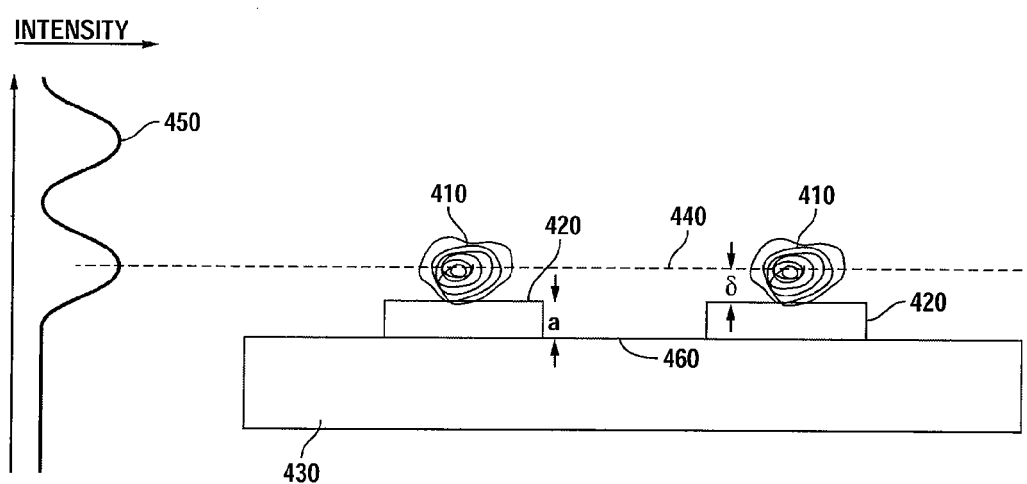
FIG. 4 is a schematic drawing illustrating the detection of an object comprising multiple fluorophores on an optimized substrate comprising multiple pedestals.

FIG. 4. illustrates a next aspect of the present invention for the detection of an object comprising multiple fluorophores in a three-dimensional structure on one form of an optimized substrate. In this aspect, objects to be detected 410 having a center of mass ($\delta$) are placed on raised pedestals having a thickness (a) 420 that act as a fluorescent enhancement mechanism. The fluorescent enhancement pedestals 420 are directly disposed on a reflective substrate 430. The thickness (a) of the fluorescent enhancement pedestals is designed so that when the objects 410 are placed on the substrate, the plane of maximum fluorescence 440 for a radiation (or light) pattern 450 is at the maximum intensity when using a selected incident light from an outside source. The naked surface of the reflective substrate 460 is preferably at the minimum intensity for the incident light.

Figure 5:
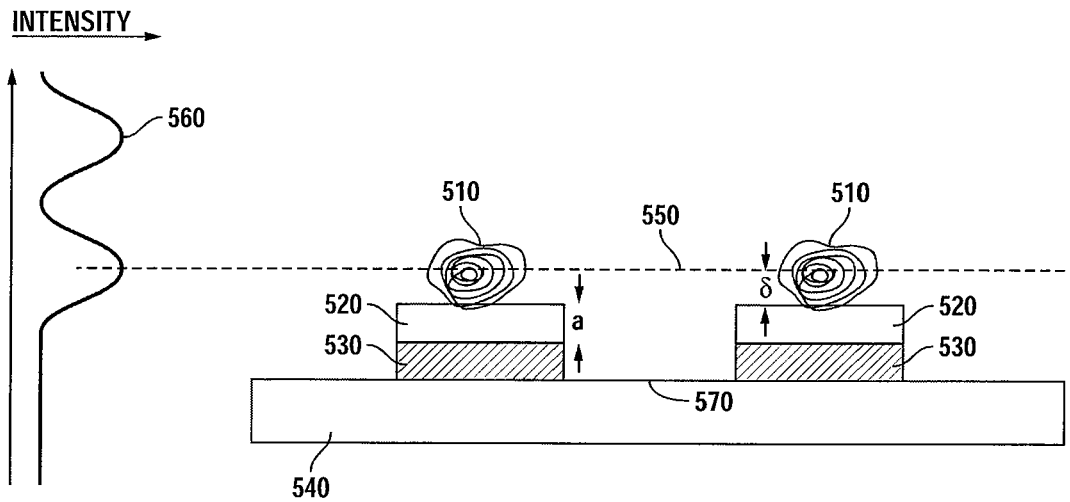
FIG. 5 is a schematic drawing illustrating the detection of an object comprising multiple fluorophores in a three-dimensional structure on an optimized substrate comprising multiple pedestals, where each pedestal comprises two or more layers.

FIG. 5 illustrates a next aspect of the present invention for the detection of an object comprising multiple fluorophores in a three-dimensional structure on an optimized substrate. In this aspect, objects to be detected 510 having a center of mass ($\delta$) are placed on raised pedestals having a thickness (a) 520 that act as a fluorescent enhancement. Each pedestal is disposed on another raised layer 530 that is a reflective substrate directly disposed on a solid base substrate 540. The thickness (a) of the fluorescent enhancement pedestals is designed so that when the objects 510 are placed on the substrate, the plane of maximum fluorescence 550 for a radiation (or light) pattern 560 is at the maximum intensity when using a selected incident light from an outside source. The naked surface of the reflective substrate 570 is preferably at the minimum intensity for the incident light. In a preferred aspect of this embodiment, the substrate 540 is preferably transparent.

Determination of Optimal Enhancement Factors

As seen in FIGS. 1-5, when the proper fluorescence enhancement thickness (a) is provided, the plane of maximum fluorescence for the objects is located at or near an antinode of the standing wave which is established above the transparent coating when the stimulating light beam is reflected. The antinode is ideally the first antinode of the average of all standing wave of wavelengths of interest, since the separation of standing waves of various wavelengths is minimal at that plane. The location of the center of mass ($\delta$) in this embodiment is indicated as the plane of maximum fluorescence. In these aspects of the invention, optimal fluorescence occurs with maximum excitation. Even if the coating thickness is not exactly correct for the specific excitation wavelength, if the intensity is only 90% or 95% of the peak intensity, the fluorescence signal will still be significantly improved over prior art sample substrates. Variations from the ideal thickness can occur due sample-to-sample variation and coating variations, or due to an averaging of the plane of maximum fluorescence due to the use of two or more fluorophores.

Figure 6:
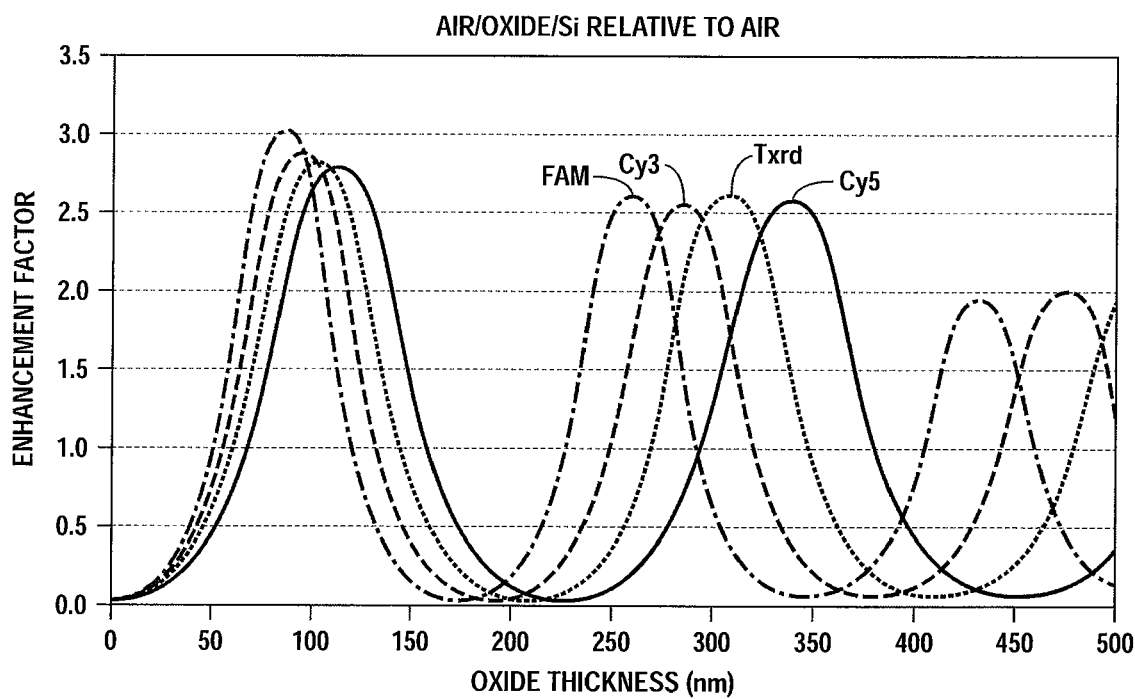
FIG. 6 is a schematic drawing illustrating the theoretical variations of fluorescence enhancement factor in air as a function of dielectric layer thickness for four common fluorescent probes at the $SiO_2/Si$ surface assuming zero thickness of the fluorophore-containing objects.
Figure 7:
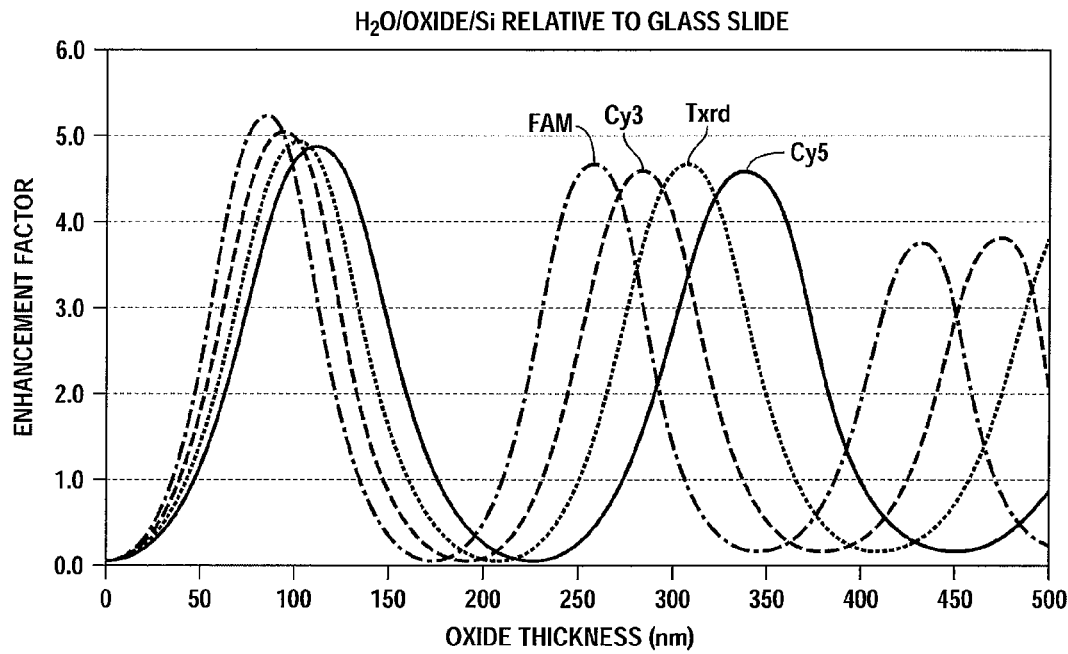
FIG. 7 is a schematic drawing illustrating the theoretical variations of fluorescence enhancement factor in water as a function of dielectric layer thickness for four common fluorescent probes at the $SiO_2/Si$ surface relative to a glass slide in an aqueous setting assuming zero thickness of the fluorophore-containing objects.
Figure 8:
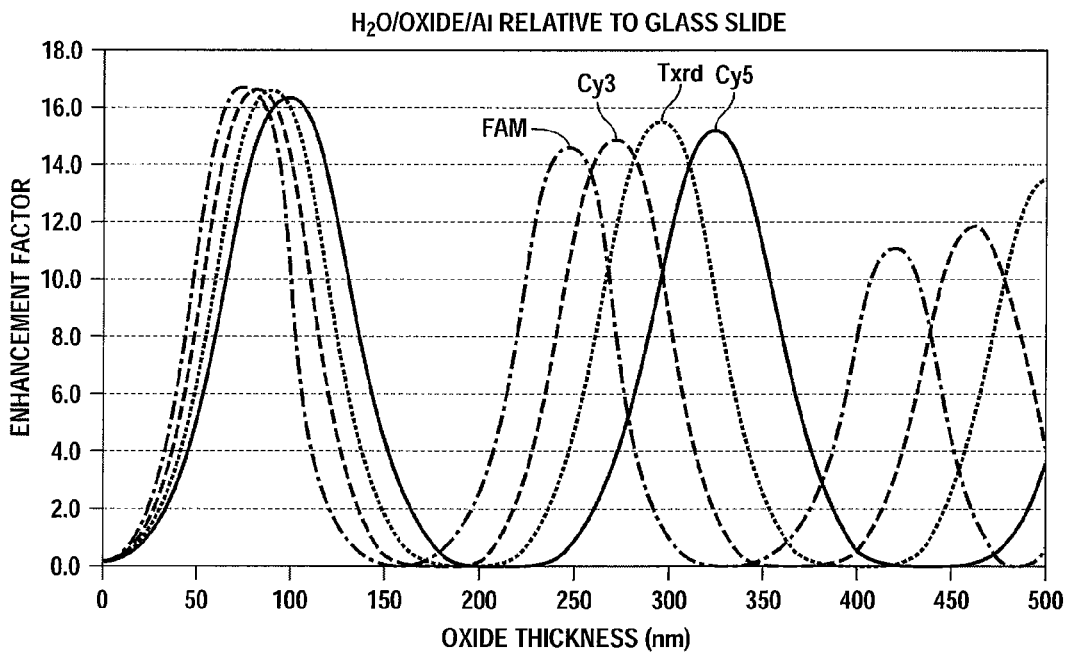
FIG. 8 is a schematic drawing illustrating the theoretical variations of fluorescence enhancement factor in water as a function of dielectric layer thickness for four common fluorescent probes at the $SiO_2/Al$ surface relative to a glass slide in an aqueous setting assuming zero thickness of the fluorophore-containing objects.

The theoretical variations of enhancement factor as a function of fluorescence enhancement layer thickness can be calculated for fluorescent probes based on the surface interfaces of the device and the conditions under which the detection is to occur. FIGS. 6-8 provide examples of such calculations for four common fluorophores—FAM, Cy3, Texas Red, and Cy5—in different settings assuming zero thickness of the fluorophore-containing object. FIG. 6 is a schematic drawing illustrating the theoretical variations of absorbance enhancement factor as a function of dielectric layer thickness at a $SiO_2/Si$ surface relative to air in an air setting. FIG. 7 illustrating the theoretical variations of absorbance enhancement factor as a function of dielectric layer thickness at a $SiO_2/Si$ surface relative to a glass slide in an aqueous setting. FIG. 8a is a schematic drawing illustrating the theoretical variations of absorbance enhancement factor as a function of dielectric layer thickness at the $SiO_2/Al$ surface relative to a glass slide in an aqueous setting.

Typically there is an inherent difference of signal intensity for different fluorophores, as can be seen in FIGS. 6-8. In specific aspects of embodiments, the thickness (a) is optimized to the average of the greatest signal intensity of the fluorophores to be detected to enhance the detection. An optimum fluorescence layer thickness (a) to accommodate two or more excitation wavelengths can be calculated based on the theoretical optimal thicknesses for each fluorophores to be detected and taking an average.

The devices of the invention are designed to work with any compatible fluorescence imaging system. The devices according to the present invention are constructed to maximize fluorescent emission and collection relative to a non-optimized substrate without having to increase the power of the laser beam (typically configured as a single-wavelength excitation source) and without having to change the objective or other optics in the system other than the device substrate itself. For example, the devices of the invention can be used with fluorescence microscope systems, including those described in U.S. Pat. No. 4,284,897 to Sawamura et al., U.S. Pat. No. 5,091,652 to Mathies et al., U.S. Pat. No. 5,296,700 to Kumagai, U.S. Pat. No. 5,381,224 to Dixon et al., U.S. Pat. No. 5,504,336 to Noguchi, U.S. Pat. No. 5,672,880 (Ser. No. 08/616,174) to Kain, U.S. Pat. No. 5,847,400 (Ser. No. 08/791,684) to Kain et al., and U.S. Pat. No. 5,646,411 (Ser. No. 08/595,355) to Kain et al.

The fluorescence imaging system could have one or more light sources providing multiple fluorescence excitation wavelengths, either simultaneously or selectably, for different fluorescent sample constituents. The nominal optical thickness distribution of the multilayer coating needs and can then be optimized for each of the different excitation wavelengths in parallel for the same multilayer coating.

For example, when two excitation wavelengths are defined by the fluorophores used with the devices of the invention (e.g., Cy5 at 633 nm and Cy3 at 532 nm), the thickness (a) of the sample substrate can be determined to provide an average plane of maximum fluorescence so as to optimize the combined detection of both of these fluorophores. The resulting average plane of maximum fluorescence will not provide the optimized structure for one or the other fluorophore, but rather the best approximate distance to be used in calculating the optimal substrate structure for detection of both. Designing the substrate for these aspects of the invention will thus need to take into account the differences in wavelength of the two fluorophores used as well as the fluorophore distribution in or on the object to be detected.

EXAMPLES

The following examples are put forth so as to provide those of ordinary skill in the art with a complete disclosure and description of how to make and use the present invention, and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Efforts have been made to ensure accuracy with respect to numbers used (e.g., amounts, temperature, etc.), but some experimental errors and deviations should be accounted for.

Example 1

Enhancing the Fluorescence Signal from a Labeled DNA: Concatamer Using a $SiO_2$/Si Substrate The following example provides the calculation and construction of a sample substrate optimized to provide detection of fluorophores distributed through a plurality of DNA concatamers comprising approximately 1 Kb of nucleotides in a single-stranded, three dimensional construct attached to a $SiO_2$/Si substrate. The production of such concatamers is described, for example, in U.S. patent application Ser. No. 11/451,691, which is published Patent Application 2007/0099208 assigned to the assignee of the present invention.

For the present example, the finite average size of the DNA concatamers was factored into the calculation of the substrate construction to provide maximal detection of each DNA concatamer.

Figure 9:
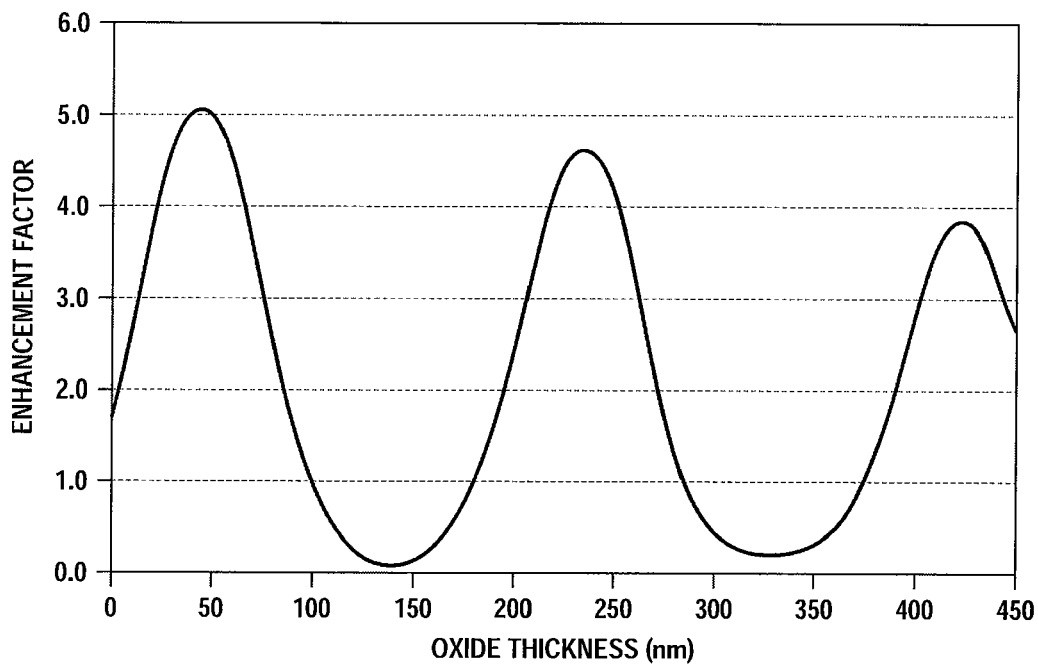
FIG. 9 is a schematic drawing illustrating the calculated enhancement for a silicon substrate coated with a $SiO_2$ layer as a function of the thickness of the oxide film using the fluorophore Cy3, assuming the center of mass of the object is displaced about 50 nm from the surface.

FIG. 9 displays a plot of the calculated total enhancement for a silicon substrate coated with a $SiO_2$ layer as a function of the thickness of the oxide film, with a fluorophore-containing object that has a center of mass of approximately 50 nm above the surface. The enhancement factor was normalized for the signal expected from a glass substrate. As shown in the graph, the maximum enhancement occurs at a thickness of about 50 nm, which roughly corresponds to a quarter of the wavelength in the fluorescent enhancement layer minus 50 nm.

Figure 10:
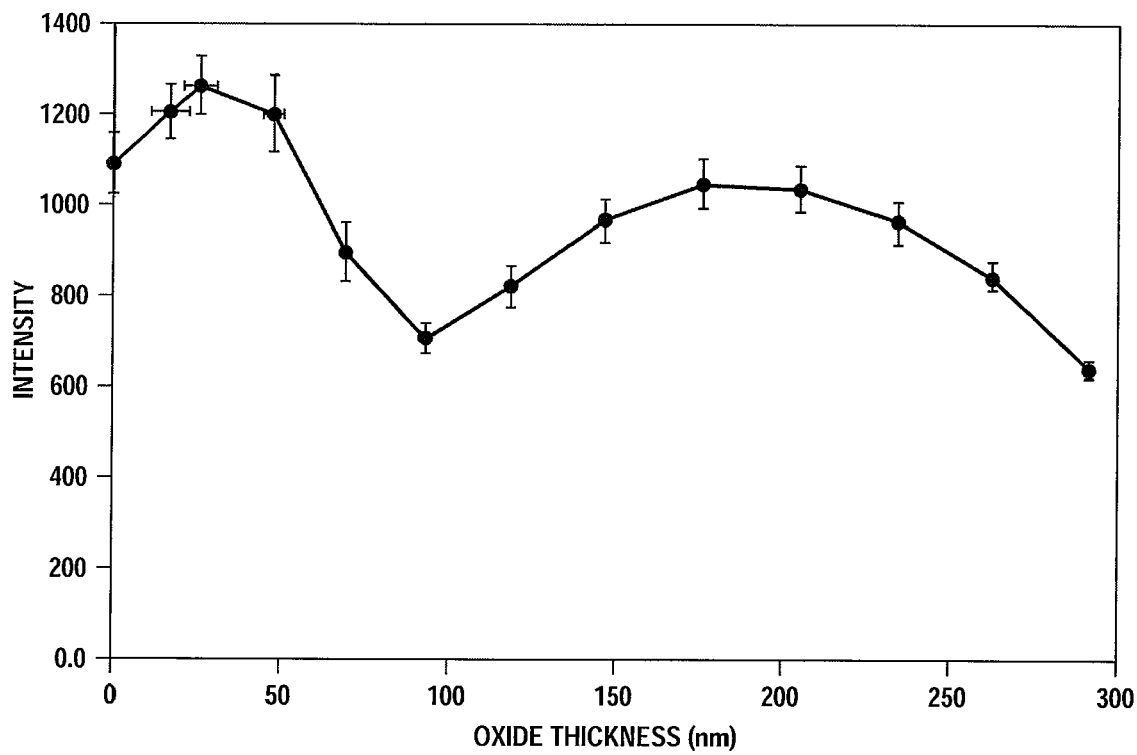
FIG. 10 is a graph of experimental data illustrating the maximal fluorescent signal intensity as a function of oxide thickness for DNA concatamers on a $SiO_2/Si$ surface.

Experimental data was then obtained for a $SiO_2$/Si substrate having a plurality of DNA concatamers comprising multiple fluorophores distributed throughout the molecule attached to the substrate surface. As seen in FIG. 10, the maximal fluorescent signal intensity as a function of oxide thickness for the DNA concatamers attached to the surface occurs at a thickness of 30 nm. The downward shift in peak position is due to the average finite thickness of the DNA concatamers, which in this case is 60 nm.

Example 2

Enhancing the Fluorescence Signal from a Labeled DNA: Concatamer Using a $SiO_2$/Al Substrate The following example provides the calculation and construction of a sample substrate optimized to provide detection of fluorophores distributed through a plurality of DNA concatamers comprising approximately 1 Kb in a single-stranded, three dimensional construct attached to a $SiO_2$/Al substrate. For the present example, the finite average size of the DNA concatamers, 60 nm, was factored into the calculation of the substrate construction to provide maximal detection of each DNA concatamer.

Figure 11:
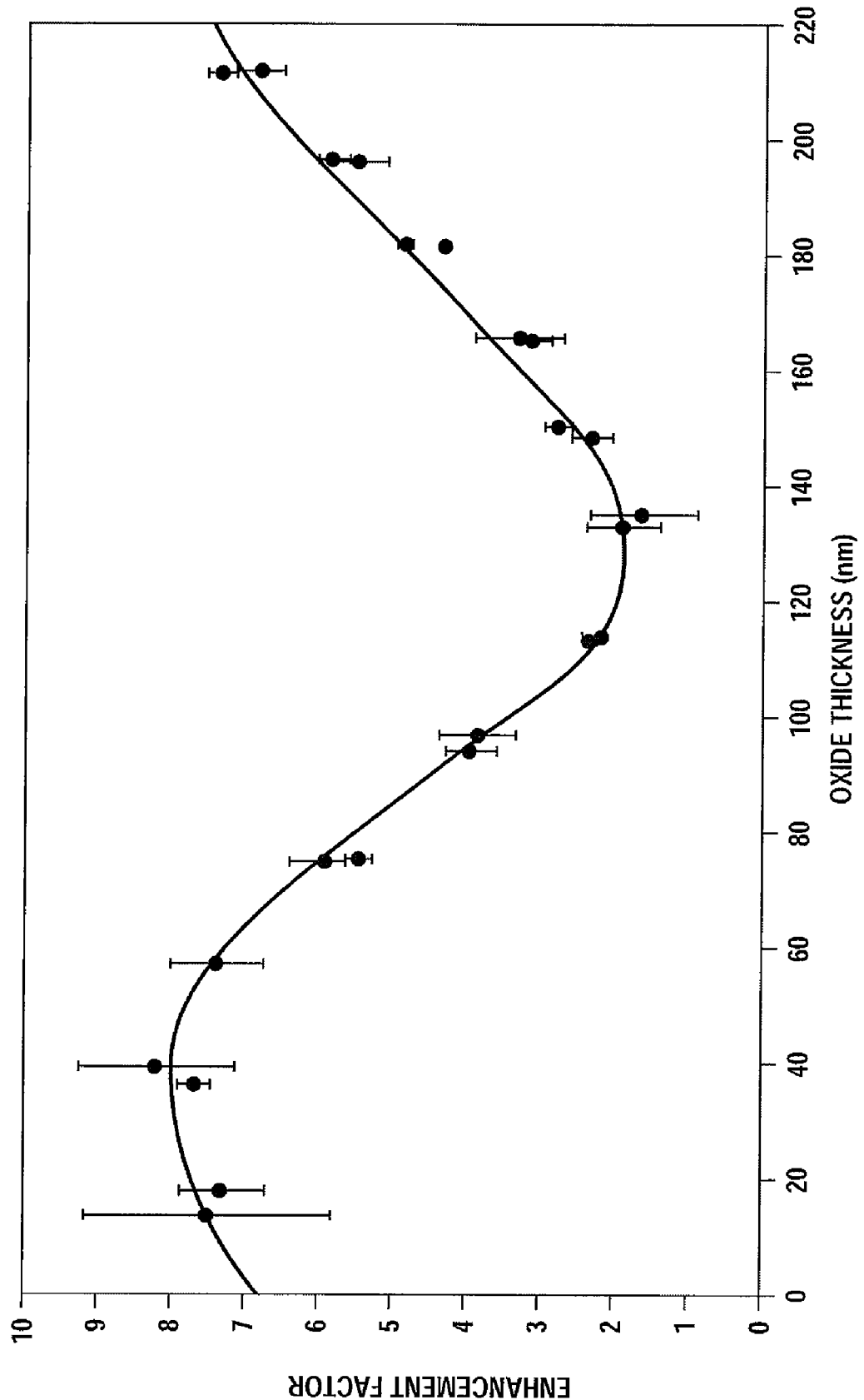
FIG. 11 is a graph of experimental data illustrating the maximal fluorescent signal intensity as a function of oxide thickness for DNA concatamers on a $SiO_2/Al$ surface.

Experimental data was obtained for a $SiO_2$/Al substrate having a plurality of DNA concatamers comprising multiple Cy3 fluorophores distributed throughout the molecule attached to the substrate surface. As seen in FIG. 11, the maximal fluorescent signal intensity as a function of oxide thickness for such concatamers attached to the surface occurs at a thickness of 45 nm, which was found empirically to be different than the optimal thickness using Si, as demonstrated in Example 1.

While this invention is satisfied by embodiments in many different forms, as described in detail in connection with preferred embodiments of the invention, it is understood that the present disclosure is to be considered as exemplary of the principles of the invention and is not intended to limit the invention to the specific embodiments illustrated and described herein. Numerous variations may be made by persons skilled in the art without departure from the spirit of the invention. The scope of the invention will be measured by the appended claims and their equivalents. The abstract and the title are not to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. §112, ¶6.

What is claimed is:

1. A device for enhancing fluorescence detection comprising:
    a reflective substrate; and
    a fluorescence enhancement layer on the reflective substrate for receiving a plurality of fluorophore-comprising objects, the fluorophore-comprising objects having a nominal radial thickness $\delta$ to the center of mass;
    wherein the fluorescence enhancement layer is of a thickness a optimized for the detection of the fluorophore-comprising objects based on a defined plane of maximum fluorescence for the objects, the defined plane of maximum fluorescence being at a separation from the reflective substrate corresponding to a combined thickness $a+\delta$, the separation being equal to substantially one-quarter of the wavelength $\lambda$ of a weighted average of peaks of absorption spectrum and emission spectrum of the fluorophore-comprising object divided by the refractive index of the fluorescence enhancement layer.

2. The device of claim 1, wherein the fluorescence enhancement layer is a dielectric material.

3. The device of claim 1, wherein the reflective substrate comprises alternating dielectric materials having relatively higher and lower refractive indices.

4. The device of claim 1, wherein the reflective substrate comprises a metal.

5. The device of claim 1, wherein the substrate comprises a substrate base and a metal coating.

6. The device of claim 1, wherein the reflective substrate comprises silicon.

7. The device of claim 4, wherein the reflective substrate comprises aluminum.

8. The device of claim 4, wherein the reflective substrate comprises titanium.

9. The device of claim 1, wherein the thickness of the fluorescence enhancement layer is optimized for the detection of at least two fluorophores of different excitation wavelengths and emission wavelengths.

10. A device for enhancing fluorescence detection comprising:
   a reflective substrate; and
   a fluorescence enhancement layer on the reflective substrate for receiving a plurality of fluorophore-comprising objects of non-zero thickness;
   wherein the fluorescence enhancement layer is of a thickness optimized for the detection of the fluorophore-comprising objects based on a defined plane of maximum fluorescence for the objects, wherein the fluorescence enhancement layer comprises a plurality of depressions, each depression being of a breadth comparable with the size of individual fluorophore-containing objects, the depressions being disposed within the enhancement layer for receiving placement of the individual fluorophore-comprising objects at the depth in the enhancement layer optimized so that the plane of maximum fluorescence of the objects is at an intensity maximum for detection of the fluorophores, and the top surface of the enhancement layer is located at an intensity minimum so as to enhance signal to background noise.

11. The device of claim 10, wherein the depressions comprise a plurality of wells each of a breadth comparable to the fluorophore-comprising objects formed within raised areas of a material different from the material of the enhancement layer for receiving placement of the fluorophore-comprising objects upon the fluorescence enhancement layer at the depth optimized so that the plane of maximum fluorescence of the objects is at an intensity maximum for detection of the fluorophores and the raised areas are located at an intensity minimum so as to enhance signal to background of the device.

12. A device for enhancing fluorescence detection, comprising:
   a reflective substrate;
   a fluorescence enhancement layer comprising a plurality of raised areas of a breadth comparable in size to individual fluorophore-comprising objects, each said raised area for receiving a plurality of the fluorophore-comprising objects of non-zero thickness, the fluorophore-comprising objects being of a radial thickness $\delta$ to the center of mass;
   wherein the objects are disposed on said raised areas, and where the placement of the objects on the fluorescence enhancement layer is at a thickness a that is optimized so that the plane of maximum fluorescence of the objects is at an intensity maximum for detection of the fluorophores, the plane of maximum fluorescence being at a separation from the reflective substrate corresponding to the thickness plus the radius $a+\delta$, the separation being equal to substantially one-quarter of the wavelength $\lambda$ of a weighted average of peaks of absorption spectrum and emission spectrum of the fluorophore-comprising object divided by refractive index of the fluorescence enhancement layer, the raised areas and the placement to enhance signal to background noise at each object.

13. The device of claim 12, wherein the reflective substrate comprises alternating dielectric materials having relatively higher and lower refractive indices.

14. The device of claim 12, wherein the thickness of the fluorescence enhancement layer is optimized for the detection of two or more fluorophores.

15. The device of claim 12 wherein each of the plurality of raised areas is formed of a separate fluorescence enhancement layer.

16. The device of claim 12, wherein the reflective substrate is a solid support.

17. A device for enhancing fluorescence detection, comprising:
   a solid substrate;
   a plurality of pedestals of non-zero thickness on said solid substrate for supporting fluorophore-comprising objects, the fluorophore-comprising objects having a nominal radial thickness $\delta$ corresponding to a center of mass; and
   a reflective substrate between said pedestals and said solid substrate;
   said pedestals designated as a fluorescence enhancement layer of thickness-a optimized for the detection of the fluorophore-comprising objects based on a defined plane of maximum fluorescence for the objects,
   the plane of maximum fluorescence being at a separation from the reflective substrate corresponding to a combined thickness $a+\delta$, the separation being equal to substantially one-quarter of the wavelength $\lambda$ of a weighted average of peaks of absorption spectrum and emission spectrum of the fluorophore-comprising object divided by the refractive index of the fluorescence enhancement layer in order to enhance signal to background noise at each said object.

* * * * *